United States Patent
Refai et al.

(10) Patent No.: US 8,142,435 B2
(45) Date of Patent: Mar. 27, 2012

(54) MULTI-FUNCTIONAL SURGICAL INSTRUMENT AND METHOD OF USE FOR INSERTING AN IMPLANT BETWEEN TWO BONES

(75) Inventors: Daniel Refai, Saint Louis, MO (US); Jeffrey A. Farris, Berne, IN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 531 days.

(21) Appl. No.: 12/388,581

(22) Filed: Feb. 19, 2009

(65) Prior Publication Data

US 2010/0211119 A1    Aug. 19, 2010

(51) Int. Cl.
*A61B 17/70* (2006.01)

(52) U.S. Cl. ............... 606/86 A; 606/99; 606/90

(58) Field of Classification Search ........ 606/86 A, 606/90, 99, 279; 623/17.15
See application file for complete search history.

(56) References Cited

U.S. PATENT DOCUMENTS

| | | | |
|---|---|---|---|
| 2,333,033 A | 10/1943 | Mraz | |
| 4,157,715 A | 6/1979 | Westerhoff | |
| 4,289,123 A | 9/1981 | Dunn | |
| 4,386,603 A | 6/1983 | Mayfield | |
| 4,401,112 A | 8/1983 | Rezaian | |
| 4,553,273 A | 11/1985 | Wu | |
| 4,554,914 A | 11/1985 | Kapp et al. | |
| 4,599,086 A | 7/1986 | Doty | |
| 4,636,217 A | 1/1987 | Ogilvie et al. | |
| 4,657,550 A | 4/1987 | Daher | |
| 4,877,020 A * | 10/1989 | Vich | 606/86 R |
| 4,892,546 A | 1/1990 | Kotz et al. | |
| 4,932,975 A | 6/1990 | Main | |
| 4,997,432 A * | 3/1991 | Keller | 623/17.11 |
| 5,002,576 A | 3/1991 | Fuhrmann et al. | |
| 5,236,460 A | 8/1993 | Barber | |
| 5,246,458 A | 9/1993 | Graham | |

(Continued)

FOREIGN PATENT DOCUMENTS

DE    30 23 942    1/1982

(Continued)

OTHER PUBLICATIONS

Search Report and Written Opinion for International Application PCT/US2010/022805, Dated Jun. 24, 2010.

(Continued)

*Primary Examiner* — Eduardo C Robert
*Assistant Examiner* — Lynnsy Schneider
(74) *Attorney, Agent, or Firm* — RatnerPrestia

(57) ABSTRACT

The surgical instrument includes a handle and a housing member that has a first end that is fixed to the handle and a second end that is configured to receive an engagement member. The surgical instrument also has an implant holding mechanism that is operatively associated with the housing member and the handle. The surgical instrument further includes a length control mechanism that has a knob, a rod member and a toothed member. The toothed member is fixed to one end of the rod member and the knob is attached to the other end. The surgical instrument also has a locking mechanism that includes a knob and a rod member having a proximal end to which the knob is attached and a distal end that is configured to detachably couple to a locking device. A surgical method for using the surgical instrument and a bone spacing kit is also disclosed.

35 Claims, 10 Drawing Sheets

U.S. PATENT DOCUMENTS

| | | |
|---|---|---|
| 5,281,226 A | 1/1994 | Davydov et al. |
| 5,290,312 A | 3/1994 | Kojimoto et al. |
| 5,336,223 A | 8/1994 | Rogers |
| 5,344,459 A | 9/1994 | Swartz |
| 5,405,391 A | 4/1995 | Hednerson et al. |
| 5,413,602 A | 5/1995 | Metz-Stavenhagen |
| 5,443,514 A * | 8/1995 | Steffee ........................... 128/898 |
| 5,458,641 A | 10/1995 | Ramirez Jimenez |
| 5,480,442 A | 1/1996 | Bertagnoli |
| 5,571,192 A | 11/1996 | Schonhoffer |
| 5,658,335 A * | 8/1997 | Allen ......................... 623/17.16 |
| 5,702,453 A | 12/1997 | Rabb et al. |
| 5,702,455 A | 12/1997 | Saggar |
| 5,716,415 A * | 2/1998 | Steffee ....................... 623/17.16 |
| 5,723,013 A | 3/1998 | Jeanson et al. |
| 5,776,197 A | 7/1998 | Rabb et al. |
| 5,776,198 A | 7/1998 | Rabb et al. |
| 5,800,547 A | 9/1998 | Schafer et al. |
| 5,888,223 A | 3/1999 | Bray |
| 5,916,267 A | 6/1999 | Tienboon |
| 5,989,290 A | 11/1999 | Biedermann et al. |
| 6,015,436 A | 1/2000 | Schonhoffer |
| 6,045,579 A | 4/2000 | Hochshuler et al. |
| 6,080,193 A | 6/2000 | Hochshuler et al. |
| 6,113,605 A | 9/2000 | Storer |
| 6,126,660 A | 10/2000 | Dietz |
| 6,126,674 A | 10/2000 | Janzen |
| 6,129,763 A | 10/2000 | Chauvin et al. |
| 6,159,215 A * | 12/2000 | Urbahns et al. ............. 606/86 R |
| 6,176,881 B1 | 1/2001 | Schar et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,214,050 B1 | 4/2001 | Huene |
| 6,296,665 B1 | 10/2001 | Strnad et al. |
| 6,299,644 B1 | 10/2001 | Vanderschot |
| 6,319,257 B1 * | 11/2001 | Carignan et al. ................. 606/99 |
| 6,344,057 B1 | 2/2002 | Rabb et al. |
| 6,352,556 B1 | 3/2002 | Kretschmer et al. |
| 6,375,682 B1 | 4/2002 | Fleischmann |
| 6,375,683 B1 | 4/2002 | Crozet et al. |
| 6,395,032 B1 | 5/2002 | Gauchet |
| 6,395,034 B1 | 5/2002 | Suddaby |
| 6,454,806 B1 | 9/2002 | Cohen et al. |
| 6,478,800 B1 | 11/2002 | Fraser et al. |
| 6,524,341 B2 | 2/2003 | Lang et al. |
| 6,562,074 B2 | 5/2003 | Gerbec et al. |
| 6,616,695 B1 | 9/2003 | Crozet et al. |
| 6,648,917 B2 | 11/2003 | Gerbec et al. |
| 6,660,038 B2 | 12/2003 | Boyer, II et al. |
| 6,699,246 B2 | 3/2004 | Zucherman |
| 6,719,796 B2 | 4/2004 | Cohen et al. |
| 6,723,126 B1 * | 4/2004 | Berry ........................ 623/17.11 |
| 6,730,088 B2 | 5/2004 | Yeh |
| 6,752,832 B2 * | 6/2004 | Neumann ................... 623/17.15 |
| 6,783,547 B2 | 8/2004 | Castro |
| 6,808,538 B2 | 10/2004 | Paponneau |
| 6,821,298 B1 | 11/2004 | Jackson |
| 6,835,206 B2 | 12/2004 | Jackson |
| 6,835,207 B2 | 12/2004 | Zacouto |
| 6,852,129 B2 | 2/2005 | Gerbec et al. |
| 6,863,673 B2 | 3/2005 | Gerbec et al. |
| 6,866,682 B1 | 3/2005 | An et al. |
| 6,902,579 B2 | 6/2005 | Harms et al. |
| 6,908,485 B2 | 6/2005 | Crozet et al. |
| 6,953,477 B2 | 10/2005 | Berry |
| 6,981,989 B1 | 1/2006 | Fleischmann |
| 7,022,138 B2 | 4/2006 | Mashburn |
| 7,029,498 B2 * | 4/2006 | Boehm et al. .............. 623/17.11 |
| 7,056,343 B2 | 6/2006 | Schafer et al. |
| 7,156,874 B2 | 1/2007 | Paponneau et al. |
| 7,252,673 B2 | 8/2007 | Lim |
| 7,338,526 B2 | 3/2008 | Steinberg |
| 7,384,431 B2 | 6/2008 | Berry |
| 7,674,296 B2 * | 3/2010 | Rhoda et al. ................ 623/17.15 |
| 7,918,888 B2 * | 4/2011 | Hamada ..................... 623/17.11 |
| 2001/0005796 A1 | 6/2001 | Zdeblick et al. |
| 2002/0068978 A1 | 6/2002 | Camino et al. |
| 2002/0082695 A1 | 6/2002 | Neumann |
| 2002/0161441 A1 | 10/2002 | Lang et al. |
| 2003/0045877 A1 | 3/2003 | Yeh |
| 2003/0083747 A1 * | 5/2003 | Winterbottom et al. ... 623/17.11 |
| 2004/0049271 A1 | 3/2004 | Biedermann et al. |
| 2004/0059271 A1 | 3/2004 | Berry |
| 2004/0093083 A1 | 5/2004 | Branch et al. |
| 2004/0133280 A1 | 7/2004 | Trieu |
| 2004/0153160 A1 | 8/2004 | Carrasco |
| 2004/0172129 A1 | 9/2004 | Schafer et al. |
| 2004/0181283 A1 | 9/2004 | Boyer, II et al. |
| 2004/0186569 A1 | 9/2004 | Berry |
| 2004/0186576 A1 | 9/2004 | Biscup |
| 2004/0210312 A1 | 10/2004 | Neumann |
| 2005/0060036 A1 | 3/2005 | Schultz et al. |
| 2005/0085910 A1 | 4/2005 | Sweeney |
| 2005/0090898 A1 | 4/2005 | Berry et al. |
| 2005/0113921 A1 | 5/2005 | An et al. |
| 2005/0143749 A1 | 6/2005 | Zalenski et al. |
| 2005/0187634 A1 | 8/2005 | Berry |
| 2005/0234550 A1 | 10/2005 | Metz-Stavenhagen |
| 2006/0004447 A1 | 1/2006 | Mastrorio |
| 2006/0058877 A1 | 3/2006 | Gutlin et al. |
| 2006/0058879 A1 | 3/2006 | Metz-Stavenhagen |
| 2006/0074488 A1 | 4/2006 | Abdou |
| 2006/0074490 A1 | 4/2006 | Sweeney |
| 2006/0085073 A1 | 4/2006 | Raiszadeh |
| 2006/0100710 A1 | 5/2006 | Gutlin et al. |
| 2006/0142859 A1 | 6/2006 | McLuen |
| 2006/0149371 A1 | 7/2006 | Marik |
| 2006/0200244 A1 | 9/2006 | Assaker |
| 2006/0224241 A1 | 10/2006 | Butler et al. |
| 2006/0235521 A1 | 10/2006 | Zucherman |
| 2006/0241762 A1 | 10/2006 | Kraus |
| 2006/0241770 A1 | 10/2006 | Rhoda et al. |
| 2006/0293755 A1 | 12/2006 | Lindner et al. |
| 2007/0093901 A1 | 4/2007 | Grotz |
| 2007/0129805 A1 | 6/2007 | Braddock |
| 2007/0173855 A1 | 7/2007 | Winn |
| 2007/0191954 A1 * | 8/2007 | Hansell et al. ............. 623/17.15 |
| 2007/0203490 A1 | 8/2007 | Zucherman |
| 2007/0233254 A1 | 10/2007 | Grotz et al. |
| 2007/0250171 A1 | 10/2007 | Bonin, Jr. |
| 2007/0255407 A1 | 11/2007 | Castleman et al. |
| 2007/0255408 A1 | 11/2007 | Castleman et al. |
| 2007/0255410 A1 | 11/2007 | Dickerson et al. |
| 2007/0255413 A1 | 11/2007 | Edie |
| 2007/0255421 A1 | 11/2007 | Dickson |
| 2008/0004705 A1 | 1/2008 | Rogeau et al. |
| 2008/0021555 A1 | 1/2008 | White |
| 2008/0021556 A1 | 1/2008 | Edie |
| 2008/0051896 A1 | 2/2008 | Suddaby |
| 2008/0058931 A1 | 3/2008 | White |
| 2008/0140207 A1 | 6/2008 | Olmos |
| 2008/0154305 A1 | 6/2008 | Foley |
| 2008/0167726 A1 | 7/2008 | Melkent |
| 2008/0243254 A1 | 10/2008 | Butler |
| 2008/0255574 A1 * | 10/2008 | Dye .............................. 606/99 |
| 2008/0287957 A1 * | 11/2008 | Hester et al. ................... 606/99 |
| 2008/0288073 A1 | 11/2008 | Renganath et al. |
| 2009/0030421 A1 * | 1/2009 | Hawkins et al. ................ 606/99 |
| 2009/0076610 A1 | 3/2009 | Afzai |
| 2009/0105832 A1 | 4/2009 | Allain et al. |
| 2009/0112220 A1 * | 4/2009 | Kraus ............................ 606/99 |
| 2009/0112324 A1 | 4/2009 | Refai et al. |
| 2009/0112325 A1 | 4/2009 | Refai et al. |
| 2009/0216331 A1 | 8/2009 | Grotz |

FOREIGN PATENT DOCUMENTS

| | | |
|---|---|---|
| DE | 37 29 600 | 3/1989 |
| DE | 40 12 622 | 7/1991 |
| DE | 41 09 941 | 10/1992 |
| DE | 44 09 392 | 3/1994 |
| DE | 44 23 257 | 1/1996 |
| DE | 19 500 170 | 2/1996 |
| DE | 19 509 317 | 9/1996 |
| DE | 19 519 101 | 11/1996 |

| | | |
|---|---|---|
| DE | 196 22 827 | 12/1997 |
| DE | 296 16 778 | 3/1998 |
| DE | 91 07 494 | 10/1998 |
| DE | 198 04 765 | 8/1999 |
| DE | 202 130 13 | 1/2003 |
| DE | 10 357 926 | 9/2005 |
| DE | 203 20 974 | 2/2007 |
| DE | 202008001261 U1 * | 3/2008 |
| DE | 20 2008 001 261 | 4/2008 |
| EP | 0 188 954 | 7/1986 |
| EP | 0 290 767 | 11/1988 |
| EP | 0 490 159 | 6/1992 |
| EP | 0 567 424 | 10/1993 |
| EP | 0 832 622 | 4/1998 |
| EP | 0 968 692 | 1/2000 |
| EP | 1 080 703 | 3/2001 |
| EP | 1 188 424 | 3/2002 |
| EP | 1 219 266 | 3/2002 |
| EP | 1 219 266 | 7/2002 |
| EP | 1 459 710 | 9/2004 |
| EP | 1491165 | 12/2004 |
| EP | 1 867 304 | 12/2007 |
| FR | 2 916 956 | 12/2008 |
| JP | 62 164458 | 7/1997 |
| SU | 1 560 184 | 4/1990 |
| SU | 1 739 989 | 6/1992 |
| WO | WO 92 01428 | 2/1992 |
| WO | WO 94 18913 | 9/1994 |
| WO | WO 9525486 | 9/1995 |
| WO | WO 96 17564 | 6/1996 |
| WO | WO 96 37170 | 11/1996 |
| WO | WO 97 47258 | 12/1997 |
| WO | WO 98 46173 | 10/1998 |
| WO | WO 99 39665 | 8/1999 |
| WO | WO 99 56675 | 11/1999 |
| WO | WO 99 63913 | 12/1999 |
| WO | WO 00 23013 | 4/2000 |
| WO | WO 03 096937 | 11/2003 |
| WO | WO 2004 019827 | 3/2004 |
| WO | WO 2004 026157 | 4/2004 |
| WO | WO 2004 093751 | 4/2004 |
| WO | WO 2004 052245 | 6/2004 |
| WO | WO 2004 096103 | 11/2004 |
| WO | WO 2004 100837 | 11/2004 |
| WO | WO 2005 055887 | 6/2005 |
| WO | WO 2006 065910 | 6/2006 |
| WO | WO 2007 076261 | 7/2007 |
| WO | WO 2008/065450 | 6/2008 |
| WO | WO 2008/099277 | 8/2008 |
| WO | WO 2009 058576 | 5/2009 |

OTHER PUBLICATIONS

Refai et al., PCT Search Report and Written Opinion Dated Feb. 24, 2009. PCT/US2008/080143, 14 Pgs.
PCT Search Report and Written Opinion Mailed Feb. 17, 2010. PCT/US2009/060608, 17 Pgs.
PCT Search Report and Written Opinion Mailed Feb. 23, 2009. PCT/US2008/080127, 17 Pgs.
Final Office Action dated Mar. 17, 2011 for U.S. Appl. No. 11/928,553.

* cited by examiner

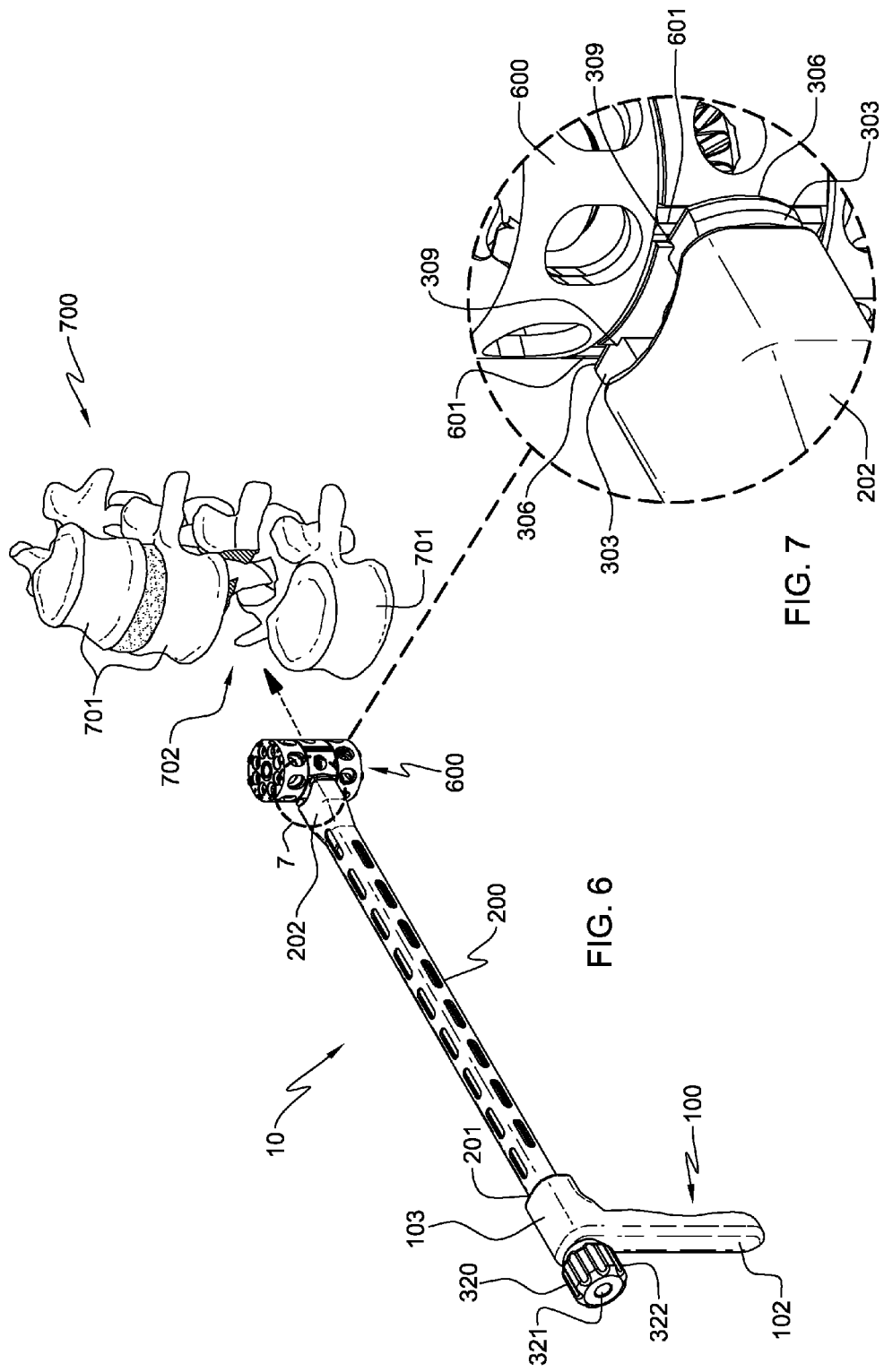

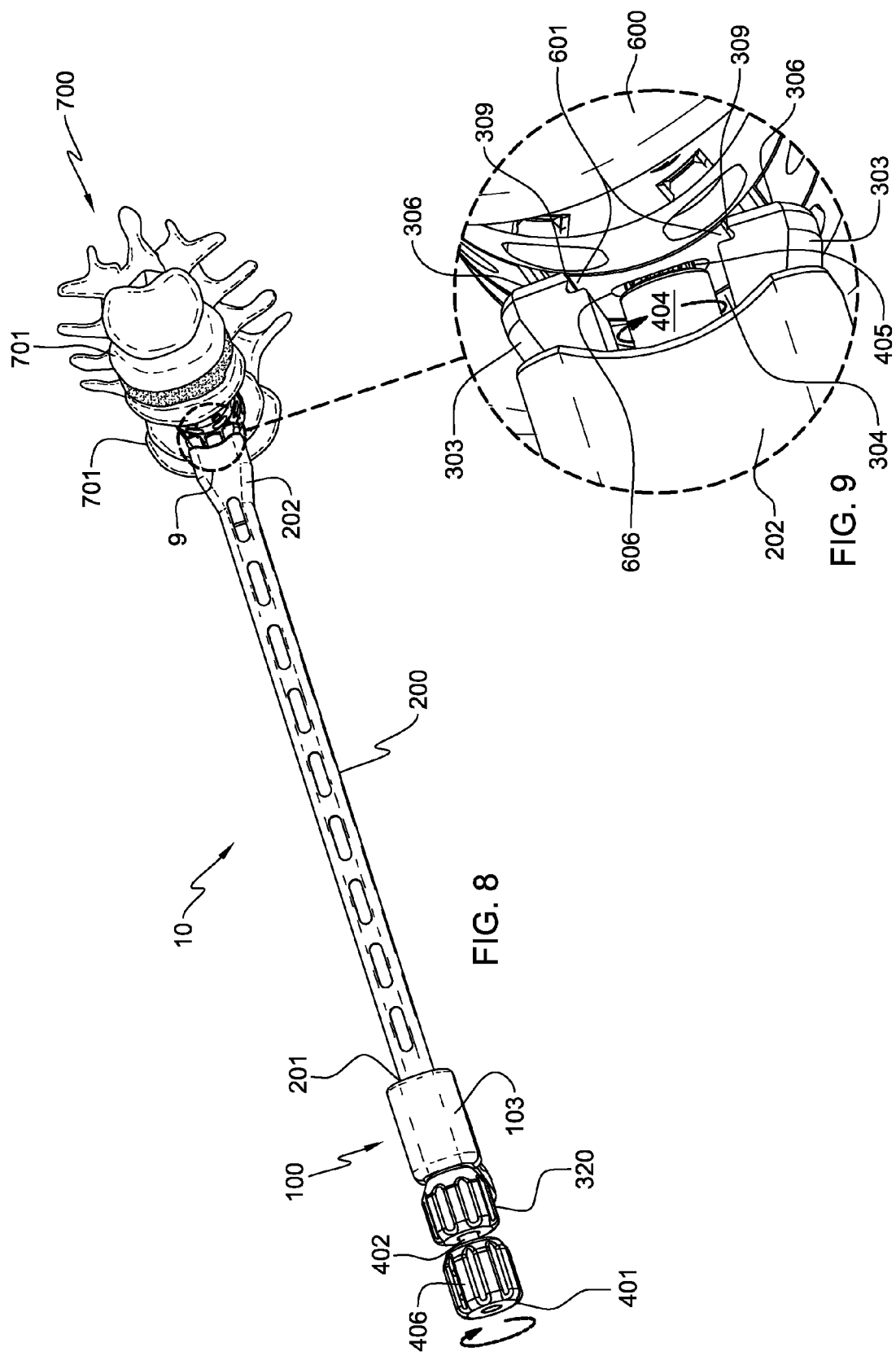

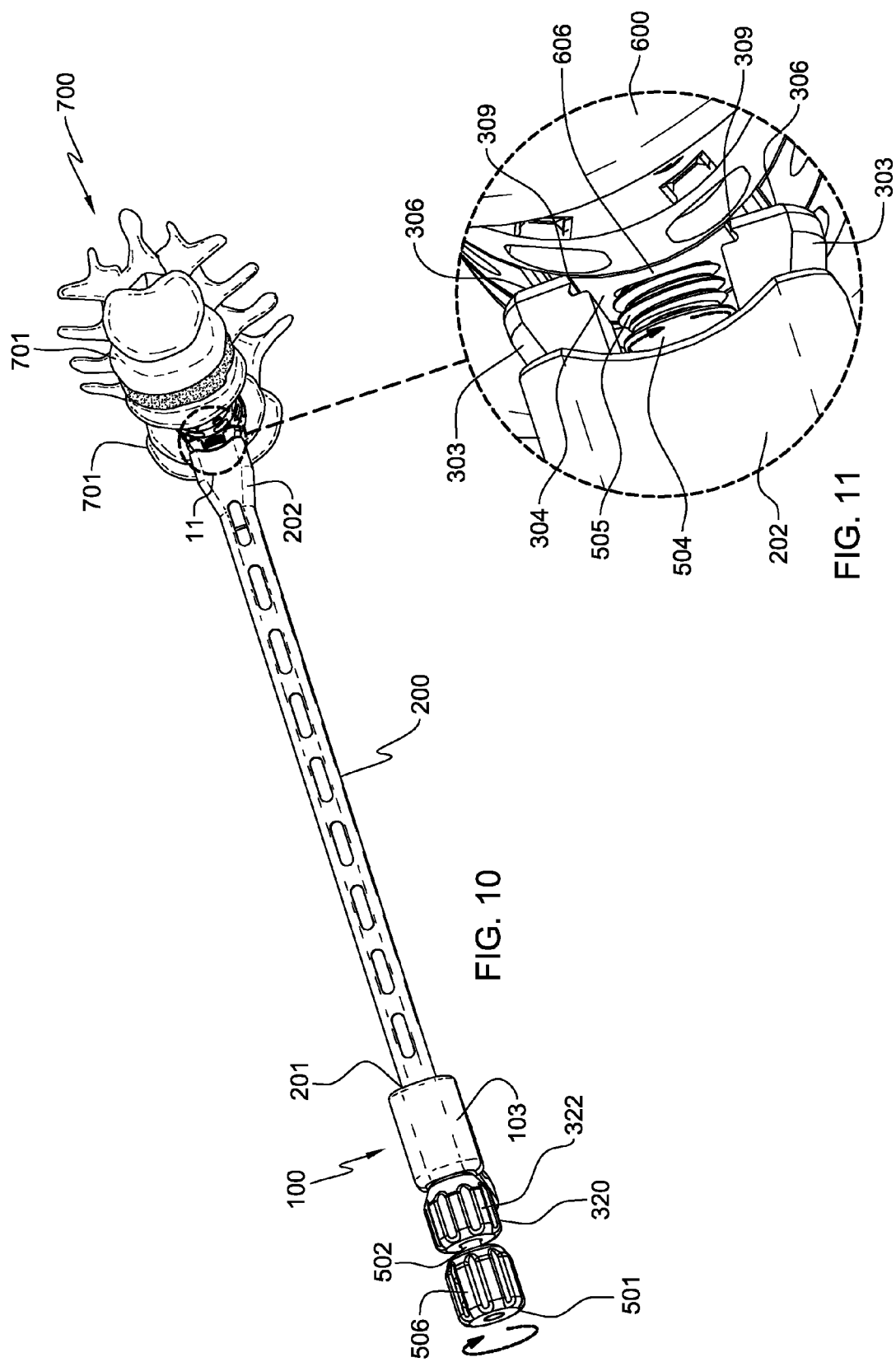

MULTI-FUNCTIONAL SURGICAL INSTRUMENT AND METHOD OF USE FOR INSERTING AN IMPLANT BETWEEN TWO BONES

TECHNICAL FIELD

The present invention relates generally to surgical instrumentation and techniques, and more specifically, but not exclusively, concerns an inserter to be used to implant a device between two hard tissue structures.

BACKGROUND OF THE INVENTION

Damage or disease that affects the integral structure of a bone structure or more specifically, a vertebral body within an individual's spinal column may lead to structural neurologic impairment with possible permanent damage to the surrounding tissue. Maintaining proper anatomic spacing within a bone structure or the spinal column is critical to ensuring continued functionality of the surrounding tissue and for the spinal column, the spinal cord and nerve roots and therefore, avoidance of long term serious neurological impairment.

Typically, spacer type of implants or more specifically, spinal implants that are used to maintain a set distance between adjacent vertebral bodies, are only available at a fixed overall length and are implanted without the ability to adjust the degree of expansion or curvature without using multiple insertion instrumentation. There remains a need for a multi-functional surgical instrument to be used to implant a spacer type of implant that allows the surgeon to manipulate and adjust the implant while in situ while limiting the size of the surgical incision, facilitating the operative technique and decreasing resultant patient morbidity.

SUMMARY OF THE INVENTION

Advancement of the state of the surgical instrumentation that are used to implant devices between two bones and more specifically, spinal implants for use in the surgical management of patients with missing or damaged vertebral bodies within an intact spinal column is desirable. The present invention satisfies the need for improvements to surgical instruments used to insert and adjust bone spacer devices and implants, but more specifically, vertebral spacer devices that are implanted in patients suffering from either diseased or damaged vertebral bodies by providing a multi-functional instrument that allows the operating surgeon to grasp, change the length and secure a variable length vertebral body replacement device following insertion into the wound site and spinal column.

The present invention provides in one aspect, a surgical instrument for inserting an implant between two bones that includes a holder member and a housing member that has a first end, a second end and a central bore that extends the length of the housing member. The first end of the housing member is attached to the holder member and the second end of the housing member is configured to receive an engagement member. The surgical instrument also includes an implant holding mechanism that is operatively associated with the housing member and the holder member. The implant holding mechanism when actuated relative to the housing member will pressingly engage and hold the implant for insertion between the two bones.

The present invention provides in another aspect, a surgical instrument that includes a handle and a housing member that has a first end, a second end and a central bore extending between the first and second ends. The first end of the housing member is fixed to the handle and the second end of the housing member is configured to receive an engagement member. The surgical instrument also includes an implant holding mechanism that is operatively associated with the housing member and the handle. The implant holding mechanism when actuated relative to the housing member will pressingly engage and hold the implant. Further included in the surgical instrument is a length control mechanism that is used to adjust the overall length of the implant. The length control mechanism has a knob, a rod member having a proximal end and a distal end and a toothed member. The toothed member is fixed to the distal end of the rod member and the knob is attached to the proximal end of the rod member. In addition, the surgical instrument has a locking mechanism for securing the overall length of the implant. The locking mechanism includes a knob and a rod member having a proximal end and a distal end. The knob is configured to attach to the proximal end of the rod member and the distal end is configured to detachably couple a locking device, with the locking device being sized and configured to be inserted into and secure the overall length of the implant after placement between the two bones.

The present invention provides in yet another aspect, a surgical method for inserting an implant between two bones. The method generally includes the step of surgically creating an opening in the skin of a patient with the opening being proximate the location of the two bones. The method further includes the step of obtaining a surgical instrument that has a handle and a housing member that includes a first end, a second end and a central bore that extends between the first and second ends. The first end of the housing member is attached to the handle and the second end of the housing member is configured to receive an engagement member. The surgical instrument also includes an implant holding mechanism that is operatively associated with the housing member and the handle. The implant holding assembly when actuated relative to the housing member will pressingly engage and hold the implant in place. The surgical instrument further includes a length control mechanism for adjusting the overall length of the implant. The length control mechanism has a knob, a rod member that includes a proximal end and a distal end and a toothed member. The toothed member is attached to the distal end and the knob is coupled to the proximal end. Additionally, the surgical instrument has a locking mechanism for securing the overall length of the implant. The locking mechanism includes a knob and a rod member that includes a proximal end and a distal end. The knob is coupled to the proximal end of the rod member and the distal end is configured to detachably couple a locking device. The locking device is sized and configured to be inserted into and secure the overall length of the implant. The surgical method may also include the step of coupling the implant to the implant holding mechanism. A further step may be to insert the surgical instrument and coupled implant into the surgical opening. Another additional step may include positioning the implant into the space between the two bones. The surgical method usually includes the further steps of changing the length of the implant to cause the implant to contact the two bones and then, securing the length of the inserted implant.

Yet a further aspect of the present invention provides bone spacing kit that includes an implant for placement between two bones and a surgical instrument. The surgical instrument usually includes a handle and a housing member that has a first end, a second end and a central bore that extends between the first and second ends. The housing member is fixed to the handle with the second end of the housing member being configured to receive an engagement member. The surgical instrument also includes an implant holding mechanism that is operatively associated with the housing member and the handle. The implant holding assembly when actuated relative to the housing member will pressingly engage the implant. The surgical instrument will also have a length control mechanism for adjusting the overall length of the implant. The length control mechanism will include a knob, a rod member having a proximal end and a distal end and a toothed member. The toothed member is attached to the distal end of the rod member and the knob is coupled to the proximal end of the rod member. Further, the surgical instrument will include a locking mechanism for securing the overall length of the implant. The locking mechanism has a knob and a rod member that includes proximal and distal ends. The knob is typically coupled to the proximal end of the rod member and the distal end is configured to detachably couple the locking device. The locking device is sized and configured to be inserted into and secure the overall length of the implant.

Further, additional features, benefits and advantages of the present invention will become apparent from the drawings and descriptions contained therein. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

FIG. 6 is a perspective view of a spinal implant coupled to the distal end of the multi-functional surgical instrument of FIG. 1, with the implant positioned adjacent to a space between two vertebral bodies prior to insertion, in accordance with an aspect of the present invention;

FIG. 7 is an enlarged, perspective view of the distal end of the multi-functional surgical instrument of FIG. 1 showing two distal surfaces of a pair of arms of an engagement member aligned with corresponding structures disposed on the outer surface of the spinal implant, in accordance with an aspect of the present invention;

FIG. 8 is a top view of the multi-functional surgical instrument of FIG. 1 coupled to the spinal implant with the length control assembly inserted through the hole in the knob and into the central bore of the housing member with the toothed member of the length control mechanism extending into a channel of an engagement member and through an opening in the outer surface of the spinal implant, in accordance with an aspect of the present invention;

FIG. 9 is an enlarged top view of a second end of the housing member of the multi-functional surgical instrument of FIG. 1, showing the toothed member extending through the channel and into the an opening in the spinal implant to engage with a length adjustment assembly within the implant, in accordance with an aspect of the present invention;

FIG. 10 is a top view of the multi-functional surgical instrument of FIG. 1 coupled to the spinal implant with the locking mechanism inserted through the hole in the knob and into the central bore of the housing member with the locking device coupled to a distal end of a rod member and extending through the channel and into a receiving hole in the outer surface of the spinal implant, in accordance with an aspect of the present invention;

FIG. 11 is an enlarged top view of the second end of the housing member of the multi-functional surgical instrument of FIG. 1, showing the locking device extending through the channel and into the receiving hole in the outer surface of the spinal implant, in accordance with an aspect of the present invention;

DETAILED DESCRIPTION FOR CARRYING OUT THE INVENTION

Figure 1:
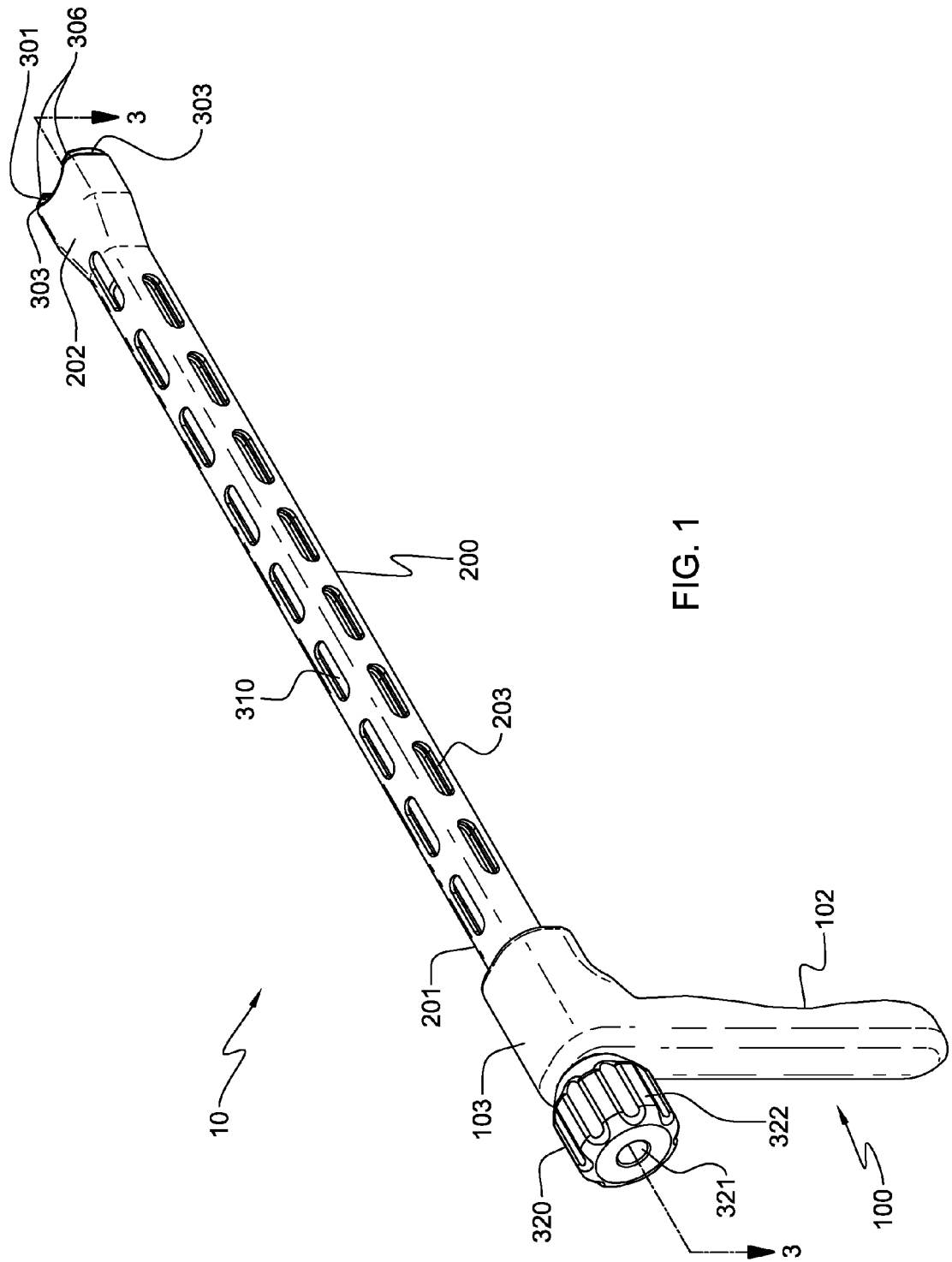
FIG. 1 is a perspective view of one embodiment of a multi-functional surgical instrument, in accordance with an aspect of the present invention.

For the purposes of promoting an understanding of the principles of the multi-functional surgical instrument, reference will now be made to the embodiments, or examples, illustrated in the drawings and specific language will be used to describe these. It will nevertheless be understood that no limitation of the scope of the invention is thereby intended. Any alterations and further modifications in the described embodiments, and any further applications of the principles of the invention as described herein are contemplated as would normally occur to one skilled in the art to which the multi-functional surgical instrument invention relates.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As used herein, the terms "multi-functional surgical instrument", "surgical instrument" and "inserter" may be used interchangeably as they essentially describe the same type of surgical instrument. Further, described herein is a surgical method for using the multi-functional surgical instrument and bone spacing kit that is used to maintain a space between two bones.

Generally stated, disclosed herein is a surgical instrument for use in inserting an implant into a space between two bones. For example purposes, the multi-functional surgical instrument is shown herein to be used to hold, extend/contract and lock a vertebral body replacement implant during implantation into the spinal column. It should be noted that other types of bone spacing implants are contemplated for use in various locations throughout the body. The multi-functional surgical instrument generally includes a holder member, a housing member and an implant holding mechanism insert through the housing member and holder member. The implant holding mechanism further includes an engagement member, a tube member and a knob with the engagement member configured to move and grasp the implant when the knob is actuated. The surgical instrument further includes a length control mechanism and locking mechanism. The distal end or toothed member of the length control mechanism is inserted through an opening in the implant and couples to a corresponding internal length adjustment mechanism to allow for varying the overall length of the implant. The surgical instrument typically also includes a locking mechanism that allows for the insertion of a locking device into the implant to fix the overall length of the implant following insertion into the space between the two bones.

Referring to FIG. 1, shown therein is a representative multi-functional surgical instrument 10, in accordance with an aspect of the present invention that includes a holder member 100, a housing member 200, and an implant engagement mechanism that includes a knob 320, a tube member 310 and an engagement member 301 having a pair of arms 303. Surgical instrument 10 is to be used to hold, adjust and secure the length of an implant that is placed between two bones in the body. One type of implant that may be used with surgical instrument 10 is the one described in co-pending U.S. patent application Ser. Nos. 11/928,532 and 11/928,553. The contents and disclosure provided in these two pending U.S. applications are hereby incorporated herein by reference.

Figure 2:
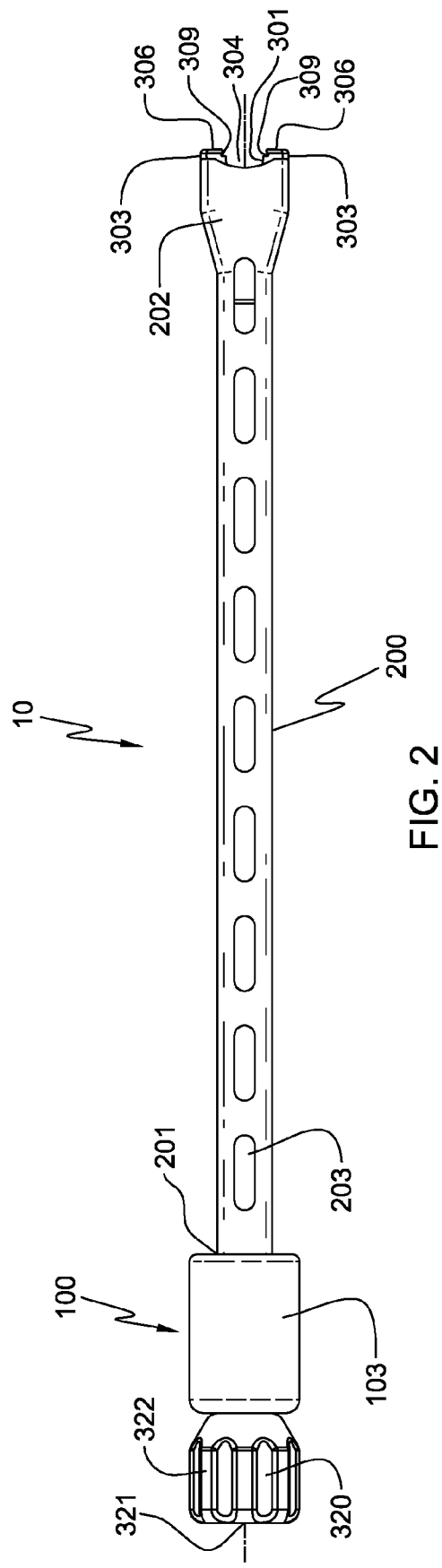
FIG. 2 is a top view of the multi-functional surgical instrument of FIG. 1, in accordance with an aspect of the present invention.

As shown in FIGS. 1 and 2, surgical instrument 10 includes holder member 100, that is shown generally as a handle, although it is contemplated that other shapes and configurations that facilitate the grasping of surgical instrument 10 may be used. Holder member 100 generally includes a grip portion 102 and a top portion 103. Grip portion 102 is shaped in a manner to allow the surgeon to be able to manipulate and maneuver the instrument with ease as well as fit various user hand sizes without sacrificing dexterity and comfort. Fixed to the distal side of top portion 103 is the first end 201 of housing member 200. Housing member 200 is generally hollow or cannulated with a central bore 203 extending the entire length of housing member 200. The second end 202 of housing member 200 is shaped to correspond to the overall shape of engagement member 301.

As seen in FIG. 2, the outer profile of second end 202 is tapered to accommodate the pair of arms 303 of engagement member 301. In addition, it is shown that pair of arms 303 each have a distal surface 306 and positioned adjacent to each distal surface 306 is a dovetail arrangement 309. Distal surface 306 is typically smooth although it is contemplated that some texturing to the surface may be used to facilitate the grasping of the implant. A channel 304 or space is created between pair of arms 303 by the overall configuration of engagement member 301.

FIGS. 1 and 2 also illustrate knob 320 being positioned adjacent to the proximal surface of top portion 103 when the assembled implant holding mechanism is placed within housing member 200. Knob 320 has a gripping portion 322 that is configured to provide to the surgeon user a non-slip surface that facilitates the actuation or rotation of knob 320 when the implant holding mechanism is used. It is contemplated that such non-slip surface may be a result of several commercially available processes including grit blasting or knurling. In addition, gripping portion 322 may be created by a molding or machining process during the manufacturing of knob 320.

Figure 3:
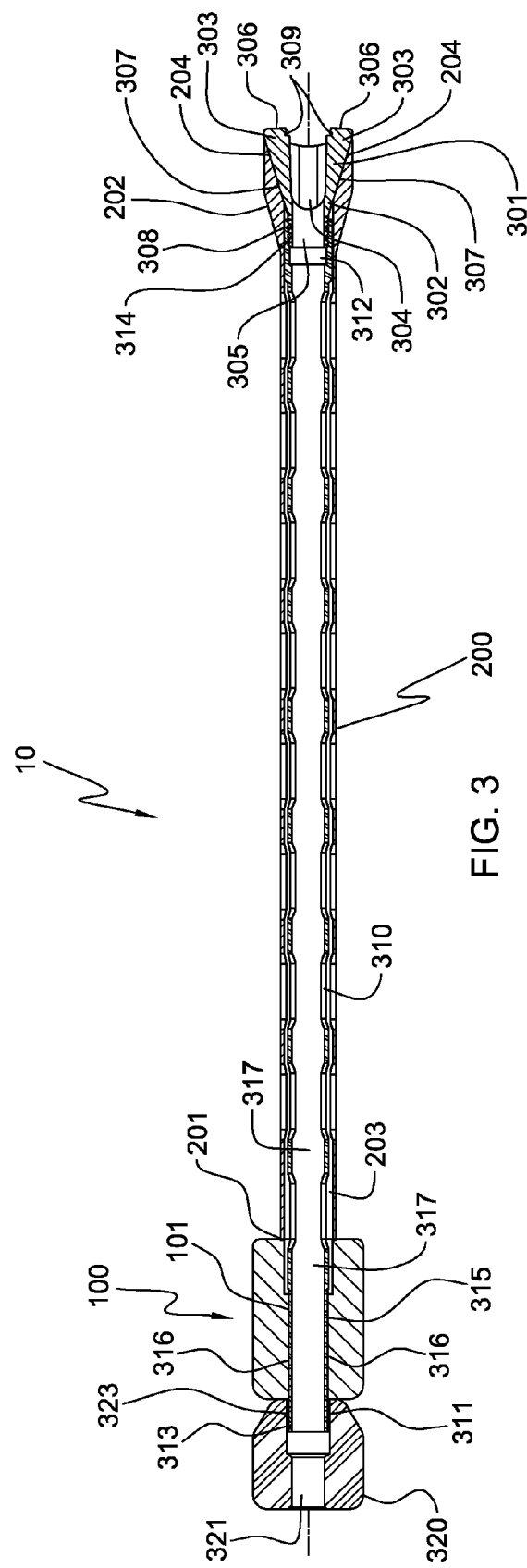
FIG. 3 is a top, sectional view of the multi-functional surgical instrument of FIG. 1 taken along line 3-3, showing an implant holding mechanism inserted through a holder member and a central bore of a housing member, in accordance with an aspect of the present invention.

Referring to FIG. 3, shown therein is a sectional view of surgical instrument 10 with the assembled implant holding mechanism inserted into housing member 200. The implant holding mechanism includes knob 320 positioned proximal to holder member 100. A hole 321 passes in a proximal to distal direction through the central portion of knob 320. A set of internal threads 323 are disposed distally on the inner surface of hole 321. Internal threads 323 are sized to engage a set of external threads 313 located at the proximal end 311 of tube member 310. The two sets of threads are configured to cause translational movement of tube member 310 when knob 320 is rotated. The implant holding mechanism also includes tube member 310 which has proximal end 311 and a distal end 312. The outer surface of proximal end 311 further includes an anti-rotation portion 315 that for the embodiment shown herein includes two generally flat surfaces 316 positioned parallel to each other on opposite sides of tube member 310. Anti-rotation portion 315 functions to generally inhibit the rotation of tube member 310 when knob 320 is threaded onto proximal end 311. This is accomplished by sliding proximal end 311 into a corresponding sized and configured hole 101 that is in top portion 103 of holder member 100. Proximal end 311 extends proximal from top portion 103 to allow for threading onto knob 320. When in operative position, flat surfaces 316 of anti-rotation portion 315 are aligned with correspondingly internal flat surfaces that are located within hole 101.

As illustrated in FIG. 3, tube member 310 extends from knob 320 within hole 101 and central bore 203 and into a portion of second end 201. The distal end 312 includes a set of internal threads 314 that configured to thread onto a set of corresponding external threads 308 of engagement member 301. The cross-sectional geometry of tube member 310 as shown is circular, but it is contemplated that other geometric shapes may be utilized. Tube member 310 is sized to fit within central bore 203 of housing member 200 and is generally hollow or cannulated with an opening 317 that extends from proximal end 311 to distal end 312.

Figure 12:
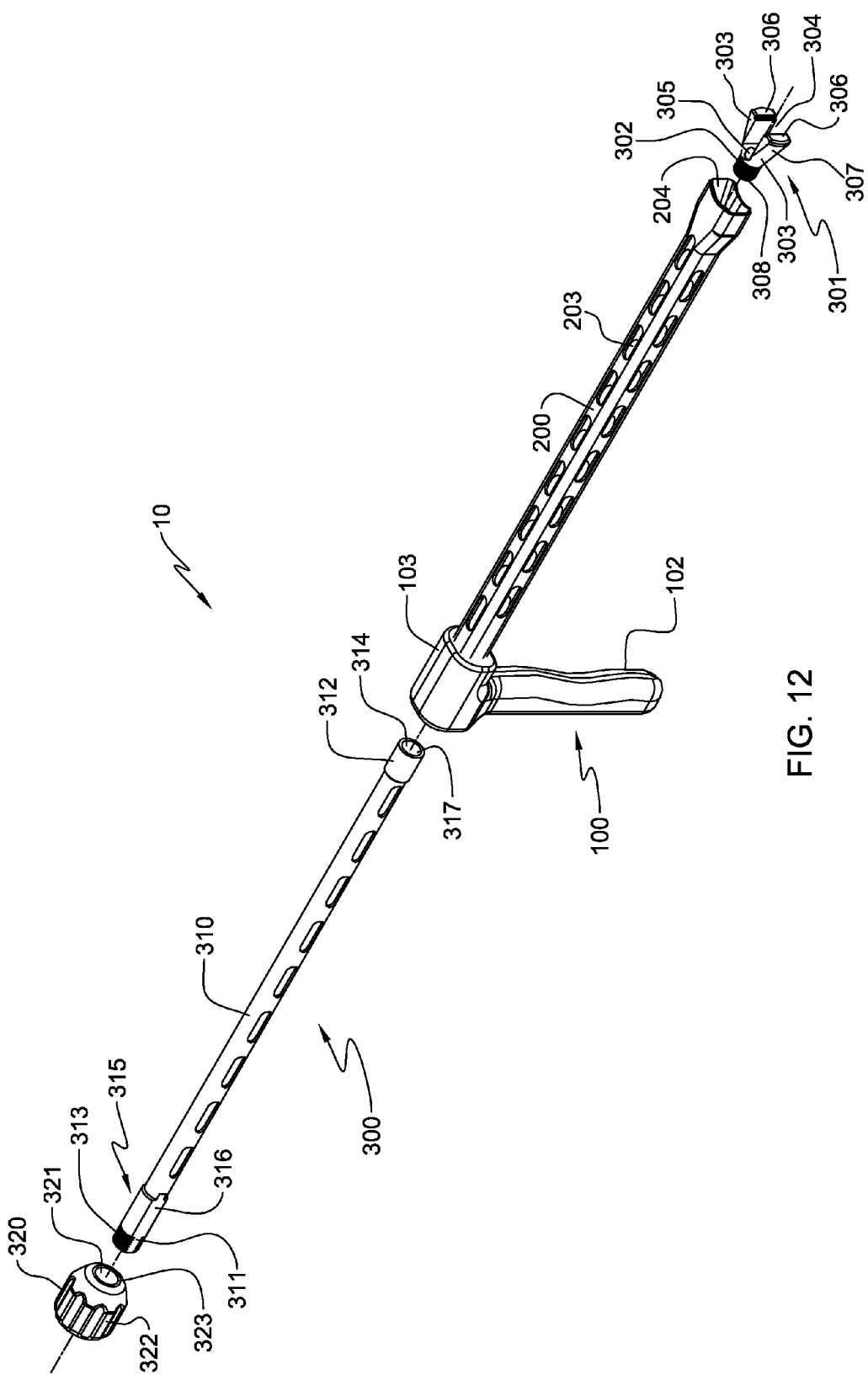
FIG. 12 is an exploded perspective view of the multi-functional surgical instrument of FIG. 1, showing an implant holding mechanism that includes a knob, a tube member and the engagement member before insertion into the holder and central bore of the housing member, in accordance with an aspect of the present invention.

The implant holding mechanism further includes engagement member 301. Referring collectively to FIGS. 3 and 12, engagement member 301 has a base 302 that includes proximally a set of external threads 308. Extending from base 302 are pair of arms 303 that define or create a channel 304 which is bordered also on one side by base 302. A through hole 305 extends from the proximal side of base 302 to and is collinear with channel 304. Hole 305 usually has a smooth inner surface to facilitate the passage of the components of the length control mechanism and the locking mechanism. Pair of arms 303 are fabricated from a material and are configured in a shape that allows for pair of arms 303 to flex inwardly and outwardly relative to channel 304. Examples of materials that may be used are various plastic polymers, flexible metals and composites. Engagement member 301 is shaped to fit into second end 202 of housing member 200. The inner surface 204 of second end 202 is tapered in the generally medial-lateral or side to side plane and the lateral or outer surfaces 307 of pair of arms 303 are configured in a similar manner to facilitate the pressing engagement of lateral surfaces 307 of pair of arms 303 to the inner surface 204 when engagement member 301 is translated in a proximal direction by tube member 310. Pair of arms 303 will move in an inwardly direction or towards each other when engagement member 301 is moved proximally relative to second end 202. In contrast, pair of arms 303 will move outwardly or away from each other when engagement member 301 moves distally relative to second end 202. The implant holding mechanism functions by the surgeon rotating knob 320. When rotated, knob 320 pressingly contacts the proximal surface of top portion 103 of holder member 100 causing tube member 310 to move in a proximal direction relative to housing member 200. Because engagement member 301 is attached to distal end 312 of tube member 310, engagement member will also move relative to second end 202 of housing member 200 member when knob 320 is rotated. As described above, typically proximal movement of engagement member 301 results in pair of arms 303 moving towards each other.

For the embodiment of surgical instrument 10 shown collectively in FIGS. 3 and 12, pair of arms 303 are each further configured to have distal surface 306 that includes a section configured as a dovetail 309 arrangement. Dovetail 309 is sized to engage corresponding holding structure (see FIG. 7) disposed on the outer surface of the implant to facilitate holding or grasping the implant when knob 320 is actuated in some fashion.

FIG. 12 is an exploded view that shows, the implant holding mechanism 300 prior to assembly and insertion into housing member 200. In the illustrated embodiment, knob 320 will be coupled to tube member 310 at proximal end 311 by the threading of internal threads 323 with external threads 313 and engagement member 301 will be coupled to distal end 312 of tube member 310 by the threading of internal threads 314 with external threads 308. For the fixation mechanism between engagement member 301 and tube member 310, it would be understood by one skilled in the art that other alternative modes of joining these two components together are contemplated, including but not limited to locking pins, locking screws, snap fits and detent mechanisms. Following assembly of the tube member-engagement member construct, tube member 310 is slid into central bore 203 of housing member 200 in a distal to proximal direction. When in operative position, proximal end 311 may extend out from top portion 103 of holder member 100 allowing for the threading of knob 320 to proximal end 311.

FIG. 6 shows surgical instrument 10 following the insertion and assembly of the implant holding mechanism within holder member 100 and housing member 200 with the implant 600 being held at second end 202 prior to being inserted into the vertebral space 702. For example purposes only, implant 600 is being shown herein as being positioned between two vertebrae 701 in the spine 700. However, it is contemplated that implant 600 may also be placed between two adjacent bone segments in other bones within the body, including, but not limited to the femur, humerus, radius, ulna, tibia and fibula.

FIG. 7 shows an enlarged view of second end 202 with pair of arms 303 extending distally therefrom and engaging implant 600. Implant 600 is shown being secured by dovetails 309 that are positioned within corresponding holding structure 601 that is disposed on the outer surface of implant 600. It is contemplated that other configurations and structures may be disposed on distal surface 306 or made part of pair of arms 303 to correspond with a reciprocal structure on the outer surface of implant 600. For example purposes only, this may include a key and slot type of configuration.

Referring collectively to FIGS. 6 and 7, to grasp implant 600 using the implant holding mechanism, the surgeon will generally rotate knob 320 causing tube member 310 (not shown) to move either distally or proximally depending on the direction of rotation. When tube member 310 moves proximally, pair of arms 303 of engagement member 301 will both move inwardly or towards channel 304 (not shown) causing dovetails 309 to pressingly engage corresponding holding structure 601 disposed on the outer surface of implant 600. For the surgeon to release implant 600, they will reverse the rotation of knob 320 which results in tube member 310 (not shown) to move in a distal direction allowing pair of arms 303 to move outwardly or away from channel 304 (not shown) allowing dovetails 309 to be released from engagement with holding structure 601.

Figure 4:
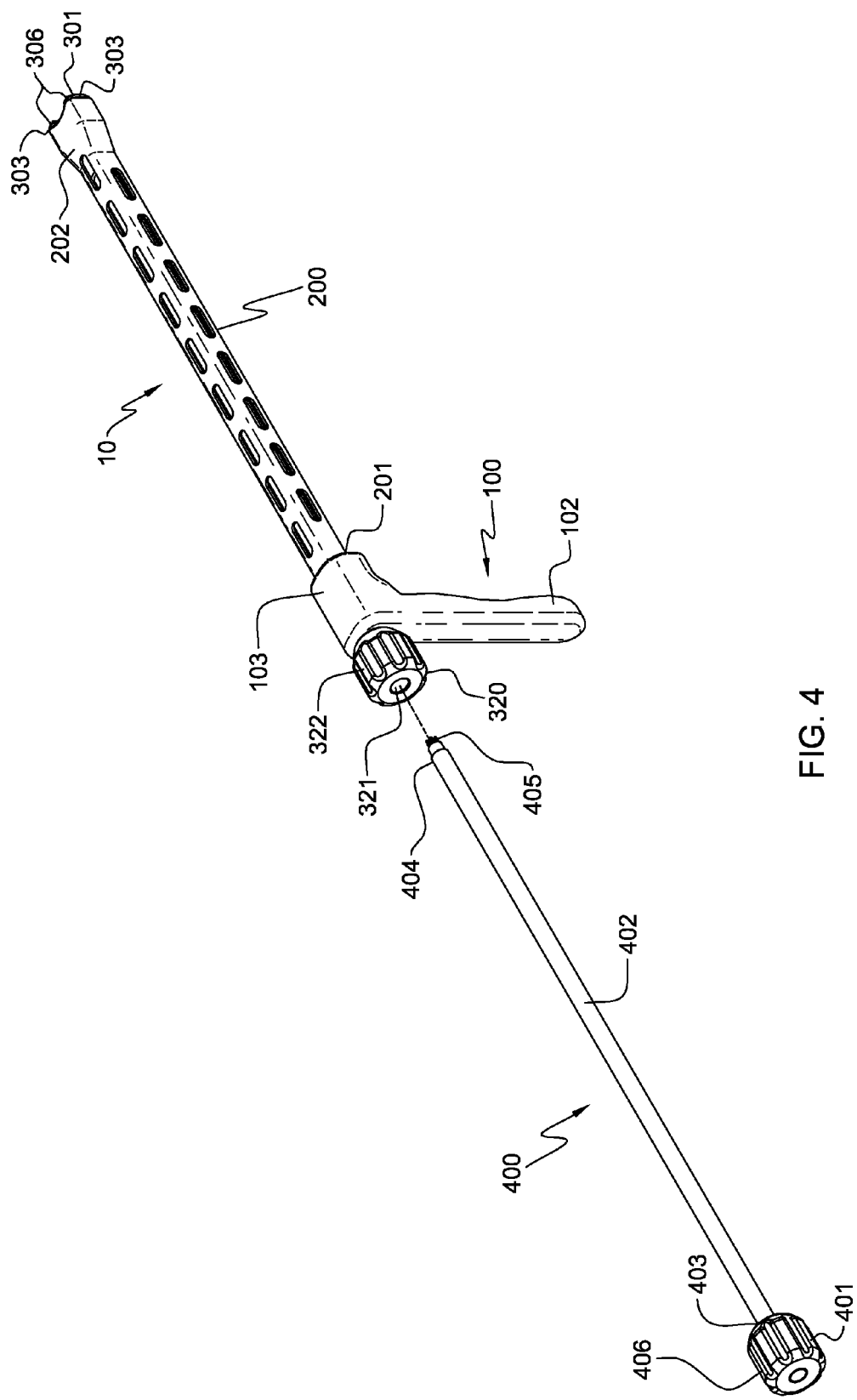
FIG. 4 is an exploded perspective view of the multi-functional surgical instrument of FIG. 1 showing a length control mechanism that includes a knob, a rod member and a toothed member positioned at a distal end of the rod member with the length control mechanism about to be inserted through the hole of the implant holding mechanism knob and into the central bore of the housing member, in accordance with an aspect of the present invention.

Referring to FIG. 4, shown therein is the length control mechanism 400 prior to insertion through hole 321 and extending into tube member 310. Length control mechanism 400 includes a knob 401 with a gripping surface 405 attached to a proximal end 403 of the rod member 402. Rod member 402 as shown, is configured as a shaft, although other types and configured constructs may be used. Positioned at the distal end 404 of rod member 402 is toothed member 405. Toothed member 405 is sized to be inserted into the implant and engage an internal length adjustment assembly (see FIG. 9) to enable the surgeon to change the overall length of the implant following positioning between two bones.

FIG. 8 shows surgical instrument 10 following the assembly and insertion of the length control mechanism through the implant holding mechanism that is already positioned within holder member 100 and housing member 200 with second end 202 proximate to implant 600. As noted previously, implant 600 is being shown herein as being positioned between two vertebrae 701 in the spine 700 for example purposes only. However, it is contemplated that implant 600 may also be placed between two adjacent bone segments in other bones within the body, including, but not limited to the femur, humerus, radius, ulna, tibia and fibula.

FIG. 9 is an enlarged view of second end 202 with pair of arms 303 extending distally therefrom and engaging implant 600. In addition, distal end 404 is shown to also extend into channel 304 with toothed member 405 being inserted into a hole 606 that is positioned in the outer surface of implant 600. Hole 606 permits toothed member 405 access to engage with the length adjustment assembly located inside implant 600. Also shown in FIG. 9 is implant 600 secured by dovetails 309 disposed on distal surface 306 of pair of arms 303 that have been positioned adjacent to corresponding holding structures 601.

Referring now collectively to FIGS. 8 and 9, to change the overall length of implant 600 using the length control mechanism 400 (shown in FIG. 4), implant 600 is initially held in position adjacent to second end 202 by the implant holding mechanism. This will then allow the surgeon to rotate knob 401 by holding gripping surface 405 causing rod member 402 to rotate within opening 317 (not shown) of tube member 310 (not shown) thereby rotating distal end 404 and attached toothed member 405. By pushing the length control mechanism distally, distal end 404 will extend into channel 304 with toothed member 405 further passing thought hole 606 and into the inner portion of implant 600 to engage the length adjustment assembly. When engaged and rotated, toothed member 405 will cause the length of implant 600 to change. The direction of rotation of knob 401 will determine whether the length of the implant is increased or decreased.

Figure 5:
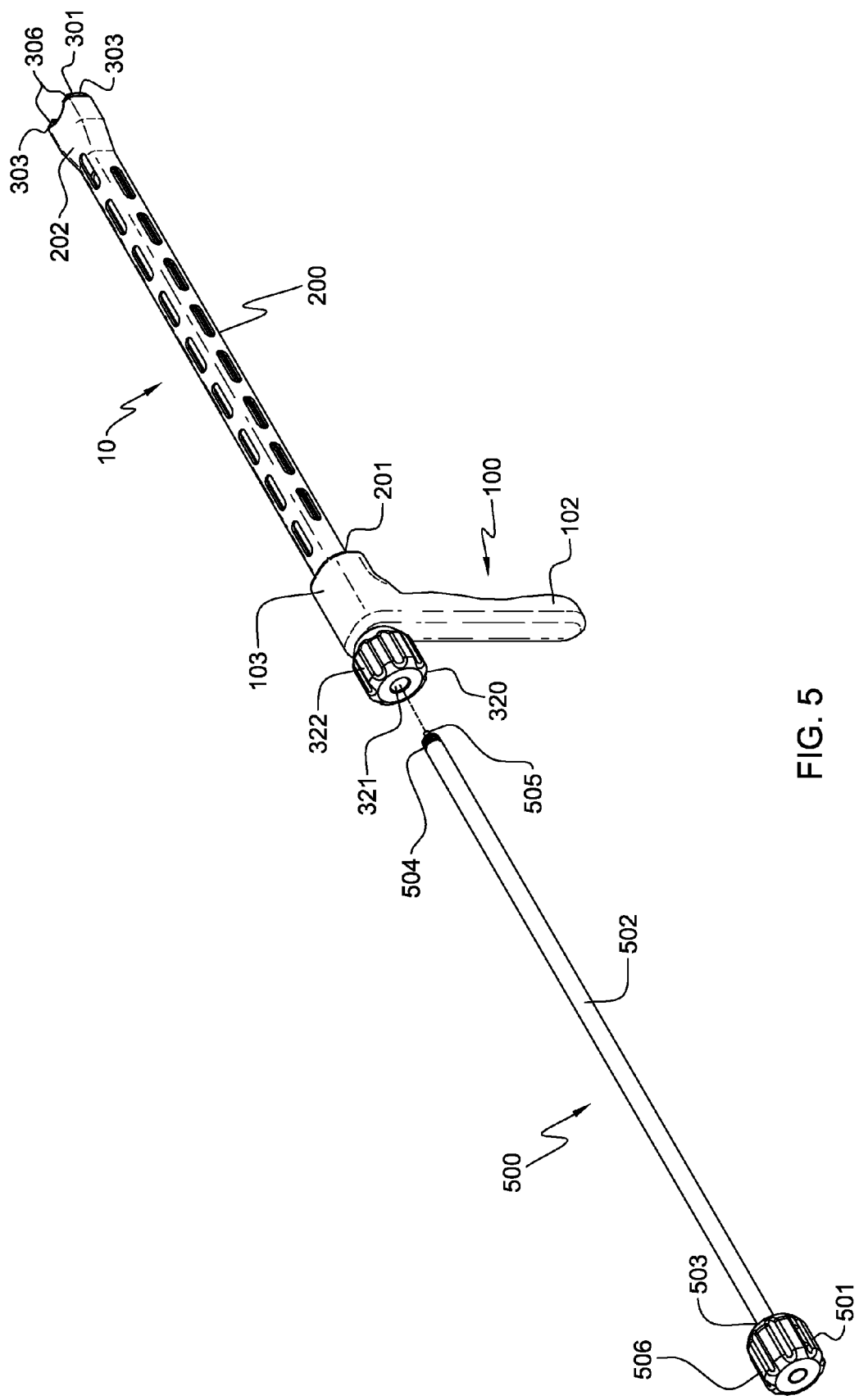
FIG. 5 is an exploded perspective view of the multi-functional surgical instrument of FIG. 1 showing a locking mechanism that includes a knob, a rod member and a locking device coupled to a distal end of the rod member, with the locking mechanism about to be inserted through the hole of the implant holding mechanism knob and into the central bore of the housing member, in accordance with an aspect of the present invention.

Shown generally in FIG. 5, is the locking mechanism 500 prior to insertion through hole 321 and extending into tube member 310. Locking mechanism 500 includes a knob 501 with a gripping surface 506 attached to a proximal end 503 of the rod member 502. Rod member 502 as shown, is configured as a shaft, although other types and configured constructs may be used. Detachably connected at the distal end 504 of rod member 502 is a locking device 505 that may be secured in some fashion to implant 600. Locking device 505 is sized to be inserted through hole 606 disposed on the outer surface of implant 600 and be secured in some manner to implant 600 (see FIG. 11). It is contemplated that locking device 505 may be screwed, press fit, latched by a detent mechanism or some other well known coupling process to either the outside part or inner portion of implant 600, thereby securing the overall length of implant 600 post-final length adjustment following placement of the implant within the space between two bones FIG. 10 shows surgical instrument 10 following the assembly and insertion of the locking mechanism through the implant holding mechanism that is already positioned within holder member 100 and housing member 200 with second end 202 proximate to implant 600. Again as noted previously, implant 600 is being shown herein as being positioned between two vertebrae 701 in spine 700 for example purposes only. However, it is contemplated that implant 600 may also be placed between two adjacent bone segments in other bones within the body, including, but not limited to the femur, humerus, radius, ulna, tibia and fibula.

FIG. 11 is an enlarged view of second end 202 with pair of arms 303 extending distally therefrom and engaging implant 600. In addition, distal end 504 is shown to also extend into channel 304 with attached locking device 505 being inserted into hole 606 that is disposed in the outer surface of implant 600. For the embodiment shown in FIG. 11, hole 606 permits locking device 505 to be inserted into implant 600 to engage either the length adjustment assembly located inside implant 600 or another structure inside the implant that will result in the securement of the overall length of implant 600. As seen in FIG. 11, locking device 505 is shown as a threaded screw member, although other embodiments are contemplated, including, but not limited to a locking pin, dowel, or plug. It is also shown in FIG. 11, implant 600 being held by dovetails 309 disposed on distal surface 306 of pair of arms 303 that have been positioned adjacent to corresponding holding structures 601.

Referring now collectively to FIGS. 10 and 11, to secure the length of implant 600 using the locking mechanism 500 (shown in FIG. 5), implant 600 is secured in position adjacent to second end 202 by the implant holding mechanism. This will then allow the surgeon to rotate knob 501 by holding gripping surface 506 causing rod member 502 to rotate within opening 317 (not shown) of tube member 310 (not shown) thereby rotating distal end 504 and detachable locking device 505. By pushing the locking mechanism distally, distal end 504 will extend into channel 304 with locking device 505 extending further into hole 606 and into the inner portion of implant 600 to engage either the length adjustment assembly or another internal structure that will result in the overall length of implant 600 being fixed. For the example shown in FIG. 11, rotation of inserted locking device 505 will result in locking device 505 being threaded into the outer surface of implant 600 or a structure positioned in the inner portion of implant 600 to engage and fix the overall length of implant 600. It is contemplated that in other embodiments of implant 600, locking device 505 may not be advanced and secured to implant 600 by threads. Alternative fixation mechanisms may include, but are not limited to, press-fit or detent arrangements. As shown in FIG. 10, it is understood that following insertion and securement of locking device 505 and while the locking mechanism remains positioned within the surgical instrument 10, the surgeon will be able to release implant 600 by reverse rotating knob 320 which results in tube member 310 (not shown) to move in a distal direction allowing pair of arms 303 to move outwardly or away from channel 304 (not shown) allowing dovetails 309 to be released from engagement with holding structure 601 and leaving the fixed length implant 600 positioned within the space 702.

Figure 13:
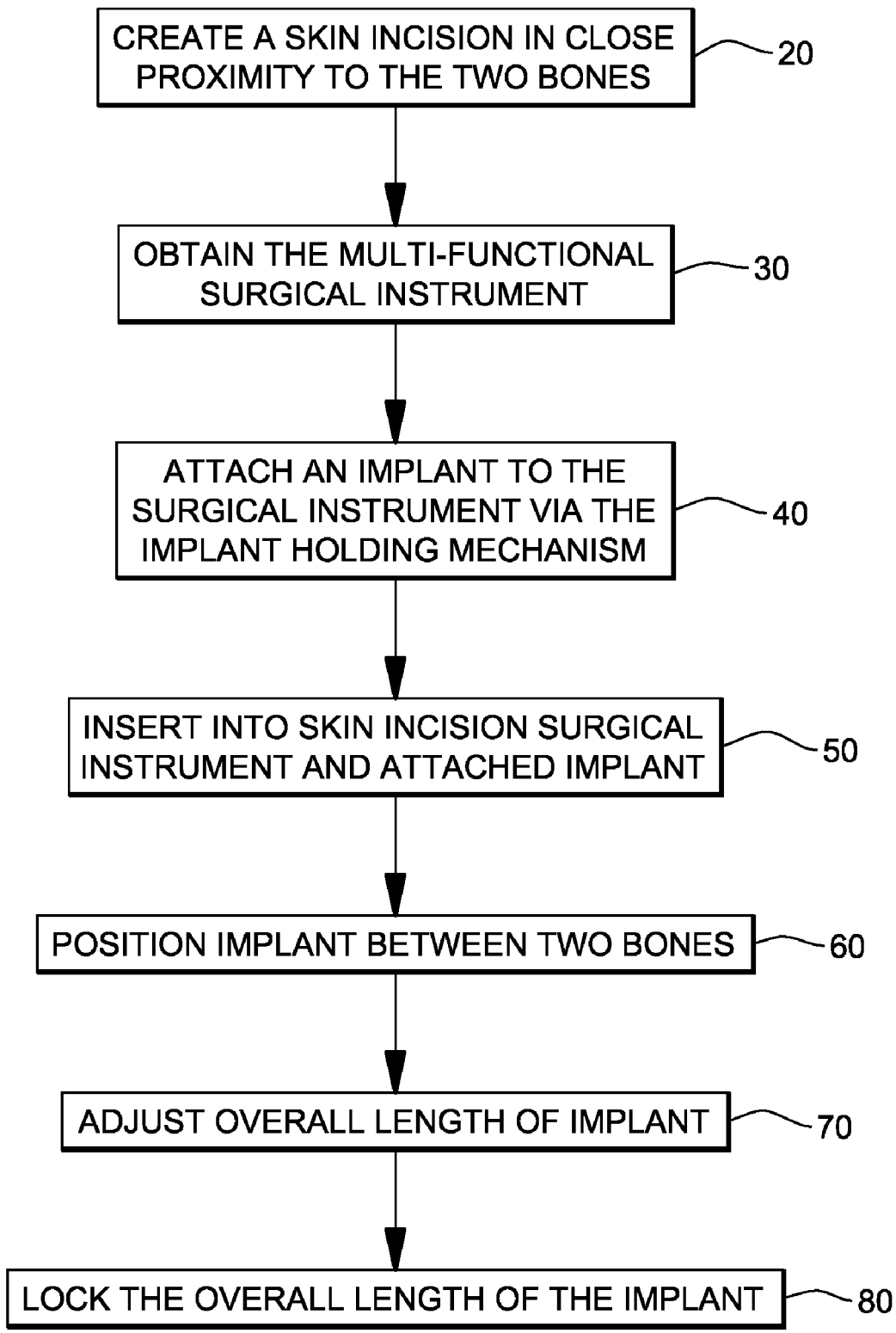
FIG. 13 is a flow chart illustrating a method according with an aspect of the present invention for inserting, expanding and locking an implant between two adjacent bones to maintain a space therebetween.

Referring to FIG. 13, the present invention also discloses a surgical method for inserting an implant between two bones. At step 20, an incision is created in the skin proximate to the target site of the two bones. A further step 30, may include obtaining multi-functional surgical instrument 10 that will generally include handle 100, a housing member 200, an implant holding mechanism 300, a length control mechanism 400 and a locking mechanism 500.

Referring collectively to FIGS. 6 and 13, at step 40, implant 600 is grasped via pair of arms 303 of implant holding mechanism 300 following the rotation of knob 320 of surgical instrument 10. At step 50, second end 202 with attached implant is inserted through the skin incision with implant 600 being positioned in close approximation to the space 702 between the two bones. Step 60 provides for implant 600 to be placed between the two bones. For example purposes, FIG. 8 shows these bones to be vertebrae 701 within spine 700. As noted above, the implant may be used in other anatomic locations in the event there is a space generated between two bone segments. Possible bones in which an implant may be used to accommodate and maintain a certain spacing include, but are not limited to the femur, humerus, radius, ulna, tibia and fibula.

Referring collectively to FIGS. 13 and 9, at step 70, the overall length of implant 600 is adjusted by rotating length control mechanism 400 following insertion into implant 600. As seen in FIG. 8, extension or contraction of the overall length of implant 600 until the two ends of implant 600 make contact with vertebrae 701 resulting in a force being applied by implant 600 to the bone surfaces of vertebrae 701 to maintain the space opening 702. The overall length of implant 600 may be extended or contracted (shortened) by rotating length control mechanism 400 either in a clockwise or counter-clockwise direction. The procedure and elements used to accomplish the changing of the overall length of implant 600 has been described above and for brevity sake will not be repeated here. As described in the above-noted pending applications that have been incorporated herein by reference, the length adjustment assembly of implant 600 is configured to convert the rotational movement of toothed member 405 into translational movement within implant 600. Essentially, when length control mechanism 400 is rotated in one direction implant 600 will extend or get longer and rotating length control mechanism 400 in the opposite direction will shorten or contract implant 600 while the implant is in place between the two bone segments. This novel functionality provides the operating surgeon with the ability to accurately adjust and ensure proper implant sizing without compromising positioning within the operative space.

Referring collectively to FIGS. 11 and 13, at step 80, the overall length of implant 600 is fixed or locked by the insertion of locking device 505 into implant 600. As seen in FIG. 11, locking mechanism 500 is rotated causing locking device 505 to engage a part of implant 600 and fix the overall length of implant 600. The procedure and elements used to accomplish the locking of the overall length of implant 600 has been described above and for brevity sake will not be repeated here.

It should be understood by those skilled in the art that the surgical method and use of surgical instrument 10 described herein may be performed using various surgical approaches including, but are not limited to, any one or combination of anterior, antero-lateral, lateral, posterior, postero-lateral, transforaminal, and/or far lateral approaches. In addition, an operating surgeon may use a minimally invasive surgical approach and employ surgical instrument 10 because of the multi-functionality (i.e., grasp, extend/contract and lock) operation of surgical instrument 10 relative to implant 600. It is further contemplated that surgical instrument 10 may be sized to allow for endoscopic insertion. Having these multiple functions incorporated into one instrument addresses a long felt need of providing the operating surgeon with the ability to keep one instrument in the wound and to not have to repeatively remove the instrument and replace it with a different instrument to perform another function. Having a multi-purpose surgical instrument will lessen the potential for tissue disruption and adjacent structural damage.

It is further contemplated that the present invention also discloses a bone spacing kit comprised of various cross-sectional sizes, cross-sectional polygonal and circular/oval shapes and longitudinal lengths of implants and a corresponding multi-functional surgical instrument 10. Surgical instrument 10 will include housing member 200 fixed to handle 100. Inserted within housing member 200 and handle 100 is implant holding mechanism 200. Implant holding mechanism includes engagement member 301 that is configured to pressingly engage implant 600 when actuated. Surgical instrument 10 further includes removable length control mechanism 400 used to adjust the overall length of implant 600. When assembled, length control mechanism is inserted into opening 317 of tube member 310 and extends into channel 304. Length control mechanism 200 includes knob 401, rod member 402 having proximal end 403 and distal end 404. Attached to distal end 404 is toothed member 405. When in use, toothed member 405 is inserted into opening 317 of tube member 310. Surgical instrument 10 further includes locking mechanism 500 that is also inserted into opening 317 of tube member 310 following the withdrawal of length control mechanism 400. Locking mechanism includes knob 501, rod member 502 that has proximal end 503 and distal end 504. Detachably connected to distal end 504 is locking device 505 that is inserted into implant 600 following final length determination. Locking device 505, which may be a set screw, locking screw, locking pin, etc. fixes and secures the overall length of implant 600 following final positioning and sizing of implant 600. For brevity sake, all of the above noted surgical instrument and implant elements will not be discussed again here and include the same structural and functionality characteristics as described previously herein.

Having a kit comprised of multiple shaped and sized modular components to construct or compliment the implant with a universal type of multi-functional instrument will allow the operating surgeon to pick and choose the modular components that are necessary to assemble an implant generally and for the example shown herein, a spinal implant, that best fits into the space between the two adjacent bones. Such flexibility also provides the surgeon with the ability to address any abnormal anatomical deformities that may be presented in a patient during the course of surgery.

Although the present surgical instrument has been described with respect to insertion of a spinal implant, it is contemplated that the surgical instrument may be sized to allow for use with various other similarly designed implants that are to be implemented in other parts of the human body.

Embodiments of the surgical instrument 10, in whole or in part, may be formed from various types of materials. Examples of such materials include, but are not limited to, reinforced polymers, stainless steel, and other durable metal or plastic composites and combinations thereof.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A surgical instrument for inserting an implant between two bones, the surgical instrument comprising:
   a holder member;
   a housing member having a proximal end, a distal end and a central bore extending there between, the proximal end of the housing member being fixed to a distal end of the holder member;
   an implant holding mechanism operatively associated with the housing member and the holder member, wherein the implant holding mechanism comprises an engagement member, a tube member and a knob, the tube member having a proximal end and a distal end with an opening extending between the proximal end and distal end of the tube member, wherein the engagement member is coupled to the distal end of the tube member and the knob of the implant holding mechanism is coupled to the proximal end of the tube member, wherein the distal end of the housing member is configured to receive the engagement member, and wherein the engagement member moves proximally relative to the distal end of the housing member when the knob of the implant holding mechanism is actuated, wherein the implant holding mechanism when actuated relative to the housing member pressingly engages and holds the implant for insertion between the two bones; and
   a length control mechanism for adjusting the overall length of the implant, the length control mechanism comprising a knob, a rod member, and a toothed member, the rod member comprising a proximal end and a distal end, the knob coupled to the proximal end of the rod member, and the toothed member fixed to the distal end of the rod member, the toothed member comprising a plurality of teeth extending from the distal end, the plurality of teeth projecting distally beyond the distal end of the housing member when the length control mechanism is inserted into the opening of the tube member.

2. The surgical instrument of claim 1, wherein the engagement member comprises a base with a hole, a pair of arms extending from the base, and a channel collinear with the hole, the channel being defined by the base and the pair of arms, with the pair of arms being configured to flex inwardly and outwardly when the engagement member is moved relative to the distal end of the housing member.

3. The surgical instrument of claim 2, wherein each of the pair of arms further comprise a distal surface, each distal surface being configured to engage a corresponding structure disposed on the implant to hold the implant after actuation of the implant holding mechanism.

4. The surgical instrument of claim 2, wherein an inner surface of the distal end of the housing member is configured to pressingly engage the pair of arms of the engagement member and flex the pair of arms in an inward direction when the engagement member is actuated in the proximal direction relative to the housing member.

5. The surgical instrument of claim 1, wherein the tube member further comprises an anti-rotation portion and the holder member includes at least one hole configured to receive the anti-rotation portion and inhibit rotation of the tube member in the holder member and housing member upon actuation of the knob of the implant holding mechanism.

6. The surgical instrument of claim 1, wherein the central bore of the housing member is sized to receive the tube member of the implant holding mechanism.

7. The surgical instrument of claim 1, wherein the toothed member is configured to mate with a length adjustment assembly in the implant, wherein when the toothed member is inserted into the length adjustment assembly in the implant and is rotated, the overall length of the implant is changed.

8. The surgical instrument of claim 1, wherein when the length control mechanism is inserted into the opening of the tube member, the knob of the length control mechanism is proximate to the knob of the implant holding mechanism and the toothed member extends into the channel of the engagement member.

9. The surgical instrument of claim 8, wherein the opening of the tube member is sized to facilitate rotation and translation of the length control mechanism following insertion into the implant holding mechanism.

10. The surgical instrument of claim 1, further comprising a locking mechanism for securing the overall length of the implant.

11. The surgical instrument of claim 10, wherein the locking mechanism is configured to be inserted into the opening of the tube member and when in an operative position, the knob of the locking mechanism is proximate to the knob of the implant holding mechanism and the distal end of the locking mechanism extends into the channel of the engagement member.

12. The surgical instrument of claim 10, wherein the opening of the tube member is sized to facilitate rotation and translation of the locking mechanism following insertion into the implant holding mechanism.

13. The surgical instrument of claim 10, wherein the locking mechanism comprises a knob and a rod member having a proximal end and a distal end, the knob of the locking mechanism being coupled to the proximal end of the rod member and the distal end of the locking mechanism being configured to detachably couple a locking device, the locking device being sized and configured to be inserted into the implant to secure the overall length of the implant.

14. The surgical instrument of claim 13, wherein the locking device is at least one of a locking pin, a locking screw, and a dowel.

15. The surgical instrument of claim 1, wherein the rod member of the length control mechanism comprises a homogeneous solid shaft.

16. A surgical instrument, the surgical instrument comprising:
 a handle;
 a housing member having a proximal end, a distal end and a central bore extending there between, the proximal end of the housing member being fixed to a distal end of the handle;
 an implant holding mechanism operatively associated with the housing member and the handle, wherein the implant holding mechanism comprises an engagement member, a tube member and a knob, the tube member having a proximal end and a distal end with an opening extending between the proximal end and distal end of the tube member, wherein the engagement member is coupled to the distal end of the tube member and the knob of the implant holding mechanism is coupled to the proximal end of the tube member, wherein the distal end of the housing member is configured to receive the engagement member, and wherein the engagement member moves proximally relative to the distal end of the housing member when the knob of the implant holding mechanism is actuated, wherein the implant holding mechanism when actuated relative to the housing member pressingly engages and holds the implant;
 a length control mechanism for adjusting the overall length of the implant, the length control mechanism comprising a knob, a rod member, and a toothed member, the rod member comprising a proximal end and a distal end, the knob coupled to the proximal end of the rod member, and the toothed member fixed to the distal end of the rod member, the toothed member comprising a plurality of teeth extending from the distal end, the plurality of teeth projecting distally beyond the distal end of the housing member when the length control mechanism is inserted into the opening of the tube member; and
 a locking mechanism for securing an overall length of the implant comprising a knob and a rod member having a proximal end and a distal end, the knob of the locking mechanism is configured to couple to the proximal end of the rod member and the distal end of the locking mechanism is configured to detachably couple a locking device, the locking device being sized and configured to be inserted into and secure the overall length of the implant after placement between the two bones.

17. The surgical instrument of claim 16, wherein the engagement member comprises a base element with a hole, a pair of arms extending from the base element, and a channel collinear with the hole, the channel being defined by the base element and the pair of arms, with the pair of arms being configured to flex inwardly and outwardly when the engagement member is moved relative to the distal end of the housing member.

18. The surgical instrument of claim 17, wherein each of the pair of arms further comprise a distal surface, each distal surface being configured to engage a corresponding structure disposed on the implant to hold the implant after actuation of the implant holding mechanism.

19. The surgical instrument of claim 17, wherein an inner surface of the distal end of the housing member is configured to pressingly engage the pair of arms of the engagement member and flex the pair of arms in an inwardly direction when the engagement member is actuated in the proximal direction relative to the housing member.

20. The surgical instrument of claim 16, wherein the tube member further comprises an anti-rotation portion and the handle includes at least one hole configured to receive the anti-rotation portion and inhibit rotation of the tube member in the handle and housing member when the knob of the implant holding mechanism is actuated.

21. The surgical instrument of claim 16, wherein the central bore of the housing member is sized to receive the tube member of the implant holding mechanism.

22. The surgical instrument of claim 16, wherein the toothed member is configured to mate with a length adjustment assembly in the implant, wherein when the toothed member is inserted into the length adjustment assembly in the implant and is rotated, the overall length of the implant is changed.

23. The surgical instrument of claim 16, wherein when the length control mechanism is inserted into the opening of the tube member, the knob of the length control mechanism is proximate to the knob of the implant holding mechanism and the toothed member extends into the channel of the engagement member.

24. The surgical instrument of claim 23, wherein the opening of the tube member is sized to facilitate rotation and translation of the length control mechanism following insertion into the implant holding mechanism.

25. The surgical instrument of claim 16, wherein the locking device is at least one of a locking pin, a locking screw and a dowel.

26. The surgical instrument of claim 16, wherein the locking mechanism is configured to be inserted into the opening of the tube member and when in an operable position, the knob of the locking mechanism is proximate to the knob of the implant holding mechanism and the distal end of the locking mechanism extends into the channel of the engagement member.

27. The surgical instrument of claim 26, wherein the opening of the tube member is sized to facilitate rotation and translation of the locking mechanism following insertion into the implant holding mechanism.

28. The surgical instrument of claim 16, wherein the rod member of the length control mechanism comprises a homogeneous solid shaft.

29. A surgical method for inserting an implant between two bones, the method comprising the steps of:
   surgically creating an opening on the skin of a patient, wherein the opening is proximate the location of the two bones;
   obtaining a surgical instrument comprising:
   a handle;
   a housing member having a proximal end, a distal end and a central bore extending there between, the proximal end of the housing member being fixed to a distal end of the handle;
   an implant holding mechanism operatively associated with the housing member and the handle, wherein the implant holding mechanism comprises an engagement member, a tube member and a knob, the tube member having a proximal end and a distal end with an opening extending between the proximal end and distal end of the tube member, wherein the engagement member is coupled to the distal end of the tube member and the knob of the implant holding mechanism is coupled to the proximal end of the tube member, wherein the distal end of the housing member is configured to receive the engagement member, and wherein the engagement member moves proximally relative to the distal end of the housing member when the knob of the implant holding mechanism is actuated, wherein the implant holding assembly when actuated relative to the housing member pressingly engages and holds the implant;
   a length control mechanism for adjusting the overall length of the implant, the length control mechanism comprising a knob, a rod member, and a toothed member, the rod member comprising a proximal end and a distal end, the knob coupled to the proximal end of the rod member, and the toothed member fixed to the distal end of the rod member, the toothed member comprising a plurality of teeth extending from the distal end, the plurality of teeth projecting distally beyond the distal end of the housing member when the length control mechanism is inserted into the opening of the tube member; and
   a locking mechanism for securing an overall length of the implant comprising a knob and a rod member having a proximal end and a distal end, the knob of the locking mechanism being coupled to the proximal end of the rod member and the distal end of the locking mechanism being configured to detachably couple a locking device, the locking device being sized and configured to be inserted into and secure the overall length of the implant;
   coupling the implant to the implant holding mechanism;
   inserting the surgical instrument and coupled implant into the opening;
   positioning the implant into a space between the two bones;
   changing the length of the implant to cause the implant to contact the two bones; and
   securing the length of the inserted implant.

30. The method of claim 29, wherein the step of coupling the implant further comprises actuating the implant holding mechanism to pressingly engage the implant with the engagement member.

31. The method of claim 29, wherein the step of changing the length of the implant further comprises inserting the toothed member into a length adjustment assembly in the implant and actuating the length control mechanism to rotate the toothed member.

32. The method of claim 29, wherein the step of securing the overall length of the inserted implant further comprises employing the locking mechanism and inserting the locking device into the implant, thereby securing the overall length of the implant.

33. The surgical method of claim 29, wherein the rod member of the length control mechanism comprises a homogeneous solid shaft.

34. A bone spacing kit, the kit comprising:
   an implant for placement between two bones; and
   a surgical instrument comprising:
   a handle;
   a housing member having a proximal end, a distal end and a central bore extending there between, the proximal end of the housing member being fixed to a distal end of the handle;
   an implant holding mechanism operatively associated with the housing member and the handle, wherein the implant holding mechanism comprises an engagement member, a tube member and a knob, the tube member having a proximal end and a distal end with an opening extending between the proximal end and distal end of the tube member, wherein the engagement member is coupled to the distal end of the tube member and the knob of the implant holding mechanism is coupled to the proximal end of the tube member, wherein the distal end of the housing member is configured to receive the engagement member, and wherein the engagement member moves proximally relative to the distal end of the housing member when the knob of the implant holding mechanism is actuated, wherein the implant holding assembly when actuated relative to the housing member pressingly engages the implant;
   a length control mechanism for adjusting the overall length of the implant, the length control mechanism comprising a knob, a rod member, and a toothed member, the rod member comprising a proximal end and a distal end, the knob coupled to the proximal end of the rod member, and the toothed member fixed to the distal end of the rod member, the toothed member comprising a plurality of teeth extending from the distal end, the plurality of teeth projecting distally beyond the distal end of the housing member when the length control mechanism is inserted into the opening of the tube member; and a locking mechanism for securing the overall length of the implant comprising a knob and a rod member having a proximal end and a distal end, the knob of the locking mechanism being coupled to the proximal end of the rod member and the distal end of the locking mechanism being configured to detachably couple a locking device, the locking device being sized and configured to be inserted into and secure the overall length of the implant.

35. The bone spacing kit of claim 34, wherein the rod member of the length control mechanism comprises a homogeneous solid shaft.

* * * * *